United States Patent
Favre et al.

(10) Patent No.: US 6,410,799 B1
(45) Date of Patent: Jun. 25, 2002

(54) HYDROFORMYLATION PROCESS EMPLOYING A CATALYST BASED ON COBALT AND/OR RHODIUM IN A NON-AQUEOUS IONIC SOLVENT

(75) Inventors: Frédéric Favre, Saint Fons; Dominique Commereuc, Meudon; Hélène Olivier-Bourbigou, Rueil-Malmaison; Lucien Saussine, Croissy sur Seine, all of (FR)

(73) Assignee: Institut Francais du Petrole, Rueil-Malmaison Cedex (FR)

( * ) Notice: Subject to any disclaimer, the term of this patent is extended or adjusted under 35 U.S.C. 154(b) by 0 days.

(21) Appl. No.: 09/935,330

(22) Filed: Aug. 23, 2001

(30) Foreign Application Priority Data

Aug. 23, 2000 (FR) .............................. 00/10971

(51) Int. Cl.$^7$ .............................. C07C 45/50
(52) U.S. Cl. .................. 568/420; 568/451; 568/909
(58) Field of Search ................ 568/451, 454, 568/909

(56) References Cited

U.S. PATENT DOCUMENTS

| | | | | |
|---|---|---|---|---|
| 4,451,679 A | * | 5/1984 | Knifton | 568/909 |
| 4,451,680 A | * | 5/1984 | Knifton | 568/909 |
| 5,874,638 A | * | 2/1999 | Chauvin et al. | 568/454 |
| 6,040,483 A | * | 3/2000 | Olivier et al. | 568/454 |
| 6,114,272 A | * | 9/2000 | Bahrmann | 502/164 |

FOREIGN PATENT DOCUMENTS

| | | |
|---|---|---|
| EP | 0 157 316 | 10/1985 |
| EP | 0 602 463 A1 | 6/1994 |
| EP | 0 776 880 A1 | 6/1997 |
| EP | 0 924 182 A1 | 6/1999 |

OTHER PUBLICATIONS

XP–000938205—Nonaqueous Room–Temperature Ionic Liquids: A New Class of Solvents for Catalytic Organic Reactions; Helene Olivier et al., pp. 249–263 (1996).

* cited by examiner

Primary Examiner—Sreeni Padmanabhan
(74) Attorney, Agent, or Firm—Millen, White, Zelano & Branigan, P.C.

(57) ABSTRACT

In a process for hydroformylation of olefinically unsaturated compounds using a catalyst based on cobalt and/or rhodium co-ordinated by at least one ligand selected from the group formed by nitrogen-containing or phosphorus-containing ligands used in a non-aqueous ionic solvent, which catalyst is liquid at a temperature of less than 90° C., in which the aldehydes formed are not or are only slightly soluble and which comprises at least one quaternary ammonium and/or phosphonium cation $Q^+$ and at least one anion $A^-$, the improvement of the invention consists in that in the cobalt and/or rhodium complex, the ligand also carries an ionic function $(Q')^+(A')^-$ where Q and Q' and/or A and A' are chemically identical.

18 Claims, No Drawings

HYDROFORMYLATION PROCESS EMPLOYING A CATALYST BASED ON COBALT AND/OR RHODIUM IN A NON-AQUEOUS IONIC SOLVENT

BACKGROUND OF THE INVENTION

1. Field of the Invention

The present invention relates to an improved process for hydroformylation of olefinically unsaturated compounds using a catalyst based on cobalt and/or rhodium used in a two-phase medium. One of the phases is constituted by a non-aqueous ionic solvent comprising at least one quaternary ammonium and/or phosphonium cation $Q^+$ and at least one anion $A^-$. The catalyst comprises at least one complex of cobalt and/or rhodium co-ordinated with at least one ligand selected from the group formed by nitrogen-containing or phosphorus-containing ligands also carrying an ionic function $(Q')^+(A')^-$ where Q and Q' and/or A and A' are chemically identical.

2. Description of the Prior Art

Hydroformylation of olefinic compounds is a reaction of great industrial importance and the majority of processes use homogeneous catalysts dissolved in an organic phase constituted by the reactants, products and possibly an excess of ligand, although difficulties are encountered in separating and recovering the catalyst, in particular when it is used in relatively large quantities, as is the case with catalysts based on cobalt, or with a noble metal, as is the case with rhodium based catalysts.

One solution to resolving that problem has been suggested by Bartik et al.: Organometallics (1993) 12 164–170, J. Organometal. Chem. (1994) 480 15–21, and by Beller et al.: J. Molecular Catal. A: Chemical (1999) 143 31–39. It consists of carrying out hydroformylation in the presence of an aqueous solution containing a cobalt complex which is rendered water-soluble by the presence of a phosphine-sulfonate ligand such as the sodium salt of trisulfonated triphenylphosphine or a trisulfonated tris-(alkylphenyl) phosphine. International patent application WO-A-97/00 132 describes clusters of cobalt substituted by trialkoxysilylmethyl groups, which render them water-soluble. In that manner, the organic phase containing the aldehydes is readily separated from the aqueous phase containing the catalyst.

A further solution to the problem has been described in U.S. Pat. No. 4,248,802. It consists of carrying out hydroformylation in the presence of an aqueous solution containing a rhodium complex which is rendered water-soluble by the presence of a sulfonated phosphine ligand which is itself water-soluble, such as the sodium salt of trisulfonated triphenylphosphine. In that manner, the organic phase containing the aldehydes is readily separated from the aqueous phase containing the catalyst. This technique has formed the subject matter of a considerable number of studies which have been discussed in an article by W. A. Herrmann in "Angewandte Chemie International", 1993, volume 32, page 1524 ff.

Despite the huge industrial interest of such techniques in the hydroformylation of propylene, such two-phase systems suffer from a lack of solubility of the olefins in water, which leads to relatively low reaction rates which renders them unsuitable for long chain olefins.

Further, United States patent U.S. Pat. No. 3,565,823 describes a technique consisting of dispersing a transition metal compound in a quaternary ammonium or phosphonium tin or germanium salt with formula $(R^1R^2R^3R^4Z)YX_3$, where $R^1$, $R^2$, $R^3$ and $R^4$ are hydrocarbyl residues containing up to 18 carbon atoms, Z is nitrogen or phosphorus, Y is tin or germanium and X is a halogen, for example chlorine or bromine. U.S. Pat. No. 3,832,391 describes a process for carbonylating olefins using such a composition. Those compositions have the disadvantage of having a relatively high melting point, for example more than 90° C., which complicates manipulation of the solutions of catalyst and reaction products.

The Applicant's patent U.S. Pat. No. 5,874,638 describes benefiting both from the advantages of two-phase processing and avoiding the disadvantages connected firstly with using water and secondly with using compounds with high melting points, by dissolving certain catalytic compounds of transition metals from groups 8, 9 or 10, known to catalyze hydroformylation, in non-aqueous ionic solvents which are constituted by organic-inorganic salts which are liquid at ambient temperature.

SUMMARY OF THE INVENTION

It has now been discovered that, in the hydroformylation reaction catalyzed by complexes based on cobalt and/or rhodium carried out in a non-aqueous ionic solvent comprising at least one quaternary ammonium and/or phosphonium cation $Q^+$ and at least one anion $A^-$, which catalyst is liquid at a temperature of less than 90° C., the amount of metal retained in the ionic solvent is greatly improved when the catalyst comprises at least one cobalt and/or rhodium complex coordinated by at least one ligand selected from the group formed by nitrogen-containing or phosphorus-containing ligands also carrying an ionic function $(Q')^+(A')^-$ where Q and Q' and/or A and A' are chemically identical.

More precisely, the invention provides a process for liquid phase hydroformylation of olefinically unsaturated compounds in which the reaction is carried out in the presence of at least one non-aqueous ionic solvent comprising at least one salt with general formula $Q^+A^-$, where $Q^+$ represents a quaternary ammonium and/or phosphonium cation, and A represents an anion, and at least one cobalt and/or rhodium complex coordinated by at least one ligand selected from the group formed by nitrogen-containing or phosphorus-containing ligands also carrying an ionic function $(Q')^+(A')^-$ where at least the cation $(Q')^+$ or anion $(A')^-$ has the same chemical nature as the cation $Q^+$ or anion $A^-$ of the non-aqueous ionic solvent.

The non-aqueous ionic solvent is selected from the group formed by liquid salts with general formula $Q^+A^-$ where $Q^+$ represents a quaternary ammonium and/or phosphonium and $A^-$ represents any anion which can form a liquid salt at low temperature, i.e., below 90° C., advantageously at most 85° C., preferably below 50° C. Preferred anions $A^-$ are nitrate, sulfate, phosphate, acetate, halogenoacetates, tetrafluoroborate, tetrachloroborate, hexafluorophosphate, hexafluoroantimonate, fluorosulfonate, perfluoroalkylsulfonates and arene-sulfonates, these latter optionally being substituted by halogen or halogenoalkyl groups.

The quaternary ammonium and/or phosphonium cations $Q^+$ preferably have general formula $NR^1R^2R^3R^{4+}$ and $PR^1R^2R^3R^{4+}$ or general formulae $R^1R^2N=C\ R^3R^{4+}$ or $R^1R^2P=C\ R^3R^{4+}$ where $R^1$, $R^2$, $R^3$ and $R^4$, which may be identical or different, represent hydrogen (with the exception of the $NH_4^+$ cation for $NR^1R^2R^3R^{4+}$), preferably a single substituent represents hydrogen, or hydrocarbyl residues containing 1 to 30 carbon atoms, for example saturated or unsaturated, cycloalkyl or aromatic alkyl groups, or aryl or aralkyl groups, which may be substituted, containing 1 to 30 carbon atoms. The ammonium and/or phosphonium cation can also be derived from nitrogen-containing and/or phosphorus-containing heterocycles containing 1, 2 or 3 nitrogen and/or phosphorus atoms, in which the cycles are constituted by 4 to 10 atoms, preferably 5 or 6 atoms.

The quaternary ammonium and/or phosphonium cation can also be a cation with formula:

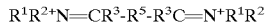

or

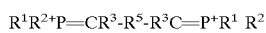

where $R^1$, $R^2$ and $R^3$, which may be identical or different, are defined as above and $R^5$ represents an alkylene or phenylene residue.

groups $R^1$, $R^2$, $R^3$ and $R^4$ include the following radicals: methyl, ethyl, propyl, isopropyl, butyl, secondary butyl, tertiary butyl, amyl, methylene, ethylidene, phenyl or benzyl; $R^5$ can be a methylene, ethylene, propylene or phenylene group.

The ammonium and/or phosphonium cation $Q^+$ is preferably selected from the group formed by N-butylpyridinium, N-ethylpyridinium, pyridinium, 3-ethyl-1-methyl-imidazolium, 3-butyl-1-methyl-imidazolium, diethylpyrazolium, N-butyl-N-methylpyrrolidinium, trimethylphenyl-ammonium, tetrabutylphosphonium and tributyl-(tetradecyl)-phosphonium. Examples of salts which can be used which can be cited are N-butyl pyridinium hexafluorophosphate, N-ethylpyridinium tetrafluoroborate, pyridinium fluorosulfonate, 3-butyl- 1-methyl imidazolium tetrafluoroborate, 3-butyl-1-methyl-imidazolium hexafluoroantimonate, 3-butyl-1-methyl-imidazolium hexafluorophosphate, 3-butyl-1-methyl-imidazolium trifluoroacetate, 3-butyl-1-methyl-imidazolium trifluoromethylsulfonate, trimethylphenylammonium hexafluorophosphate and tetrabutylphosphonium tetrafluoroborate. These salts can be used alone or as a mixture.

The cobalt and/or rhodium compound precursors of the catalyst are selected from the group formed by cobalt and/or rhodium salts such as acetylacetonates, carboxylates, in particular formate or acetate, and carbonyl compounds, such as dicobalt-octacarbonyl, cobalt-tetracarbonyl hydride, rhodium-dicarbonyl acetylacetonate and carbonyl clusters. The choice of cobalt and/or rhodium compound precursor is not critical but it is generally preferable to avoid halides.

The nitrogen-containing ligand is selected from the group formed by monoamines, di-, tri- and polyamines, imines, di-imines, pyridines, bipyridines, imidazoles, pyrroles and pyrazoles, all also containing in their formula at least one substituent carrying an ionic function $(Q')^+(A')^-$ where at least the cation $(Q')^+$ or anion $(A')^-$ has the same chemical nature as cation $Q^+$ or anion $A^-$ of the non-aqueous ionic solvent defined above.

The phosphorus-containing ligand is selected from the group formed by phosphines, polyphosphines, phosphine oxides and phosphites, all also containing in their formula at least one substituent carrying an ionic function $(Q')^+(A')^-$ such that at least the cation $(Q')^+$ or anion $(A')^-$ has the same chemical nature as cation $Q^+$ or anion $A^-$ of the non-aqueous ionic solvent defined above.

Non limiting examples of associations between the ligands and molten salts which can be cited are:

1-(4-pyridyl)2-(dicyclopentyl-methyl-phosphonium)-ethane tetrafluoroborate (1) and 1-(N-imidazolyl)-2-(dicyclopentylmethyl-phosphonium)-ethane tetrafluoroborate (2) ligands, used in ionic solvents constituted by quaternary ammonium or phosphonium tetrafluoroborates and by salts comprising dicyclopentyl-methyl-alkyl-phosphonium cations;

1-(diphenylphosphino)2-(4-N-methyl-pyridinium)-ethane hexafluorophosphate (3) ligand, used in ionic solvents constituted by quaternary ammonium or phosphonium hexafluorophosphates and by salts comprising 4-alkyl-N-methyl-pyridnium cations, the 1-(dicyclopentylphosphino)2-(3-methyl-1-imidazolium)-ethane hexafluorophosphate (4), used in ionic solvents constituted by quaternary ammonium or phosphonium hexafluorophosphates and by salts comprising 3-alkyl-1-methyl-imidazolium cations;

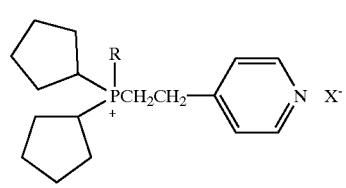

1

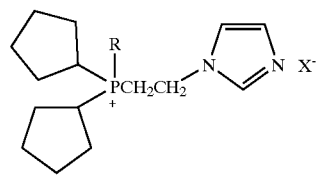

2

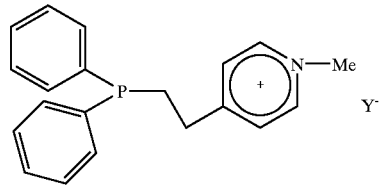

3

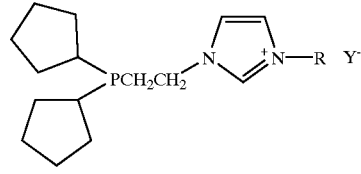

4

R = Me,  X = BF₄,  Y = PF₆

N-(3-diphenylphosphinophenyl)-N'-dimethyl-guanidinium tetrafluoroborate ligand (5), used in ionic solvents constituted by quaternary ammonium or phosphonium tetrafluoroborates and by salts comprising N-phenyl-N'-dialkyl-guanidinium cations;

tris-(tetrabutylammonium 3-phenylsulfonate)-phosphine (tetrabutylammonium triphenylphosphine trisulfonate) (6), used in ionic solvents constituted by tetrabutylammonium salts and by salts comprising sulfonate anions, such as tosylates and triflates;

tris-(sodium 3-phenyl sulfonate)-phosphine ((sodium triphenylphosphine trisulfonate) (7), used in ionic solvents constituted by salts comprising sulfonate anions, such as tosylates and triflates;

5

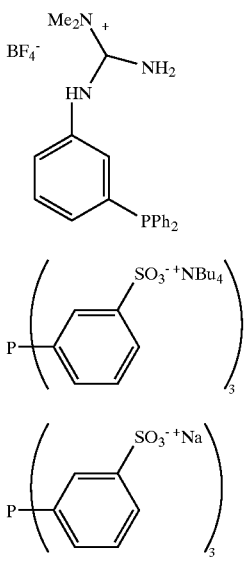

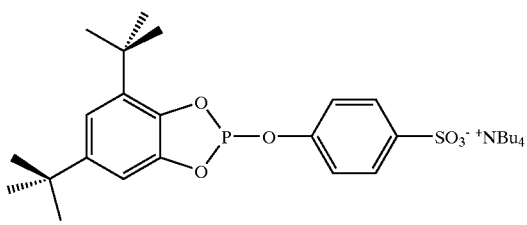

and the ligand (di-t-butyl-3,5-catecholato)-(tetrabutylammonium 4-phenoxy-sulfonate)phosphite (8), used in ionic solvents constituted by tetrabutylammonium salts and by salts comprising sulfonate anions, for example tosylates and triflates.

The catalytic composition is obtained by mixing, in any manner, the liquid salt with the cobalt and/or rhodium salt and the ligand. The transition metal compound and/or the ligand can initially be dissolved in an organic solvent.

The complex between the cobalt and/or rhodium precursor and the ligand can be prepared prior to the reaction by mixing the cobalt and/or rhodium precursor with the ligand in a suitable solvent, for example an organic solvent or the non-aqueous ionic solvent which will subsequently be used in the catalytic reaction. The complex can also be prepared in situ by mixing the cobalt and/or rhodium precursor and the ligand directly in the hydroformylation reactor.

The concentration of the cobalt and/or rhodium complex in the liquid ionic solvent is not critical. It is advantageously in the range 0.1 mmoles to 5 moles per liter of liquid ionic solvent, preferably in the range 1 mmole to 1 mole per liter, and more preferably in the range 10 to 500 mmoles per liter. The mole ratio between the ligand and the cobalt and/or rhodium compound is in the range 0.1 to 500, preferably in the range 1 to 100.

The components in the composition of the invention can be mixed in any order, at a temperature in the range −20° C. to 200° C., preferably in the range 0° C. to 140° C. and advantageously in the range 20° C. to 90° C.

The olefinically unsaturated compounds which can be hydroformylated are selected from the group formed by mono-olefins, di-olefins, in particular conjugated di-olefins, olefinic compounds comprising one or more heteroatoms, in particular from unsaturated groups such as ketone and carboxylic acid functions. Examples that can be cited are the hydroformylation of pentenes to hexanal and methylpentanal, of hexenes to isoheptanals, of isooctenes to isononanals and of $C_{10}$ to $C_{16}$ olefinic cuts to $C_{11}$ to $C_{17}$ aldehydes. These olefinic compounds can be used in the pure form or diluted with saturated hydrocarbons or other unsaturated hydrocarbons.

The ratio of the partial pressures of hydrogen and carbon monoxide used in the reaction medium for hydroformylation can be 10:1 to 1:10, preferably in a ratio of 1:1, but any other ratio can be used depending on the process.

The temperature at which hydroformylation is carried out is in the range 30° C. to 200° C., advantageously the temperature is less than 150° C., preferably in the range 50° C. to less than 150° C. The pressure can be in the range 1 MPa to 20 MPa, preferably in the range 2 MPa to 15 MPa.

The catalytic unsaturated compound hydroformylation reaction can be carried out on a closed system, in a semi-open system or batchwise using one or more reaction stages. At the reaction outlet, the organic phase containing the reaction products is advantageously separated by simple decanting of the ionic solvent phase containing the "molten salt" and the major portion of the catalyst. At least a portion of this ionic solvent phase, which contains at least a portion of the catalyst, is returned to the reactor, the other portion being treated to eliminate the catalyst residues.

The following examples illustrate the invention without limiting its scope.

EXAMPLE 1

The hydroformylation reaction was carried out in a 100 ml capacity stainless steel autoclave provided with a double envelope enabling the temperature to be regulated by circulating a heat exchange fluid. The following were introduced into this autoclave, initially purged of air and moisture and placed under a hydrogen/carbon monoxide mixture (1/1 molar) at atmospheric pressure: 0.0193 g of rhodium dicarbonyl acetylacetonate (i.e., 0.075 mmoles of rhodium), 4 mole equivalents of sodium triphenylphosphinetrisulfonate, 4 ml of 3-butyl-1-methyl-imidazolium trifluoromethylsulfonate, 2 ml of heptane (standard) and 7.5 ml of hexene-1. In this example, the sulfonate anion was the common ion of the ligand and the non-aqueous ionic solvent. The pressure of the hydrogen-carbon monoxide mixture (1/1 molar) was raised to 2 MPa and the temperature to 80° C. and stirring was commenced. After 2 hours, stirring was stopped and the reaction mixture was allowed to decant and cool, then the pressure was released. After removal from the autoclave, the upper organic phase was colorless. The hexene-1 conversion was 99% by weight. The selectivity for C7 aldehydes was 93% and the n/iso (n-heptanal/isoheptanals) ratio was 3.5. Analysis of the upper organic phase showed that it contained less than 5 ppm of rhodium metal (ppm: parts per million, by weight).

EXAMPLE 2

Comparative

The hydroformylation reaction was carried out in the same apparatus and using the same procedure as that described for Example 1. The following were introduced into this autoclave, initially purged of air and moisture and placed under a hydrogen/carbon monoxide mixture (1/1 molar) at atmospheric pressure: 0.0193 g of rhodium dicarbonyl acetylacetonate (i.e., 0.075 mmoles of rhodium), 4 mole equivalents of sodium triphenylphosphine trisulfonate, 4 ml of 3-butyl-1-methyl-imidazolium fluorophosphate, 2 ml of heptane (standard) and 7.5 ml of hexene-1. In this comparative example, there was no common ion between the ligand and the non-aqueous ionic solvent. The pressure of the hydrogen-carbon monoxide mixture (1/1 molar) was raised to 2 MPa and the temperature to 80° C. and stirring was commenced. After 3 hours, stirring was stopped and the reaction mixture was allowed to decant and cool, then the pressure was released. After removal from the autoclave, the upper organic phase was colorless. The hexene-1 conversion was 74% by weight. The selectivity for C7 aldehydes was 48% and the n/iso (n-heptanal/isoheptanals) ratio was 2.7. Analysis of the upper organic phase showed that it contained 195 ppm of rhodium metal (ppm: parts per million, by weight).

EXAMPLE 3

The hydroformylation reaction was carried out in the same apparatus and using the same procedure as that described for Example 1. 0.0193 g of rhodium dicarbonyl acetylacetonate (i.e., 0.075 mmoles of rhodium), 4 mole equivalents of sodium triphenylphosphine-disulfonate, 4 ml of 3-butyl-1-methyl-imidazolium trifluoromethanesulfonate, 2 ml of heptane (standard) and 7.5 ml of hexene-1 were introduced. In this example, the sulfonate anion was the common ion between the ligand and the non-aqueous ionic solvent. The pressure of the hydrogen-carbon monoxide mixture (1/1 molar) was raised to 2 MPa and the temperature to 80° C. and stirring was commenced. After 2 hours, stirring was stopped and the reaction mixture was allowed to decant and cool, then the pressure was released. After removal from the autoclave, the upper organic phase was colorless. The hexene-1 conversion was 98% by weight. The selectivity for C7 aldehydes was 96% and the n/iso (n-heptanal/isoheptanals) ratio was 3.5. Analysis of the upper organic phase showed that it contained less than 5 ppm of rhodium metal (ppm: parts per million, by weight).

EXAMPLE 4

The hydroformylation reaction was carried out in the same apparatus and using the same procedure as that described for Example 1. 0.0193 g of rhodium dicarbonyl acetylacetonate (i.e., 0.075 mmoles of rhodium), 10 mole equivalents of N-(3-diphenylphosphinophenyl)-N'-dimethyl-guanidinium tetrafluoroborate, 4 ml of 3-butyl-1-methyl-imidazolium tetrafluoroborate, 2 ml of heptane (standard) and 7.5 ml of hexene-1 were introduced. In this example, the tetrafluoroborate anion was the common ion between the ligand and the non-aqueous ionic solvent. The pressure of the hydrogen-carbon monoxide mixture (1/1 molar) was raised to 2 MPa and the temperature to 80° C., and stirring was commenced. After 2 hours, stirring was stopped and the reaction mixture was allowed to decant and cool, then the pressure was released. After removal from the autoclave, the upper organic phase was colorless. The hexene-1 conversion was 77% by weight. The selectivity for C7 aldehydes was 74% and the n/iso (n-heptanal/isoheptanals) ratio was 3. Analysis of the upper organic phase showed that it contained less than 5 ppm of rhodium metal (ppm: parts per million, by weight).

EXAMPLE 5

The hydroformylation reaction was carried out in the same apparatus and using the same procedure as that described for Example 1. 0.0193 g of rhodium dicarbonyl acetylacetonate (i.e., 0.075 mmoles of rhodium), 7 mole equivalents of 1-(diphenylphosphino)-2-(4-N-methyl-pyridinium)-ethane tetrafluoroborate, 4 ml of 3-butyl-1-methyl-imidazolium tetrafluoroborate, 2 ml of heptane (standard) and 7.5 ml of hexene-1 were introduced. In this example, the tetrafluoroborate anion was the common ion between the ligand and the non-aqueous ionic solvent. The pressure of the hydrogen-carbon monoxide mixture (1/1 molar) was raised to 2 MPa and the temperature to 80° C., and stirring was commenced. After 4 hours, stirring was stopped and the reaction mixture was allowed to decant and cool, then the pressure was released. After removal from the autoclave, the upper organic phase was colorless. The hexene-1 conversion was 84% by weight. The selectivity for C7 aldehydes was 99% and the n/iso (n-heptanal/isoheptanals) ratio was 2.6. Analysis of the upper organic phase showed that it contained less than 10 ppm of rhodium metal (ppm: parts per million, by weight).

EXAMPLE 6

The hydroformylation reaction was carried out in a 300 ml capacity stainless steel autoclave provided with a double envelope enabling the temperature to be regulated by circulating a heat exchange fluid, and provided with an efficient mechanical stirrer with blades and counter-blades. The following were introduced into this autoclave, initially purged of air and moisture and placed under a hydrogen/carbon monoxide mixture (1/1 molar) at atmospheric pressure: 0.4 g of dicobalt-octacarbonyl (i.e., 2.3 mmoles of cobalt), 1 mole equivalent of 1-(4-pyridyl)-2-(dicyclopentyl-methyl-phosphonium)-ethane tetrafluoroborate, 10 ml of 3-butyl-1-methyl-imidazolium tetrafluoro-borate, 30 ml of heptane and 30 ml of hexene-1. The pressure of the hydrogen-carbon monoxide mixture (1/1 molar) was raised to 9 MPa and the temperature to 95° C. and stirring was commenced. After 6 hours, stirring was stopped and the reaction mixture was allowed to decant and cool, then the pressure was released. After removal from the autoclave, the upper organic phase was slightly colored, indicating that only traces of cobalt had been extracted. The hexene-1 conversion was 80% by weight. The selectivity for C7 aldehydes was 96.4% and the n/iso (n-heptanal/isoheptanals) ratio was 3.6.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications cited above and below, and of corresponding French application 00/10971, filed Aug. 23, 2000, are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for liquid phase hydroformylation of olefinically unsaturated compounds in which the reaction is carried out in the presence of at least one non-aqueous ionic solvent comprising at least one salt with general formula $Q^+ A^-$, where $Q^+$ represents a quaternary ammonium and/or phosphonium cation, and $A^-$ represents an anion, and at least one cobalt and/or rhodium complex coordinated by at least one ligand selected from the group formed by nitrogen-containing or phosphorus-containing ligands also carrying an ionic function $(Q')^+(A')^-$ where at least the cation $(Q')^+$ or anion $(A')^-$ has the same chemical nature as the cation $Q^+$ or anion $A^-$ of the non-aqueous ionic solvent.

2. A process according to claim 1, wherein the non-aqueous ionic solvent is selected from the group formed by liquid salts with general formula $Q^+ A^-$ where $Q^+$ represents a quaternary ammonium and/or phosphonium cation and $A^-$ represents any anion which can form a liquid salt at low temperature, i.e., below 90° C.

3. A process according to claim 1, wherein the $A^-$ anion is selected from the group consisting of nitrate, sulfate, phosphate, acetate, halogenoacetates, tetrafluoroborate, tetrachloroborate, hexafluorophosphate, hexafluoroantimonate, fluorosulfonate, perfluoroalkylsulfonates, unsubstituted arene-sulfonates, and arene-sulfonates substituted by halogen or halogenoalkyl groups.

4. A process according to claim 1, wherein the quaternary ammonium and/or phosphonium cations are of the formulae $NR^1R^2R^3R^{4+}$, $PR^1R^2R^3R^{4+}$ or $R^1R^2N=C\ R^3R^{4+}$, $R^1R^2P=C\ R^3R^{4+}$ where $R^1$, $R^2$, $R^3$ and $R^4$, identical or different, represent hydrogen or hydrocarbyl residues containing 1 to 30 carbon atoms, with the proviso that the quaternary ammonium cation does not represent $NH_4^+$.

5. A process according to claim 3, wherein the quaternary ammonium and/or phosphonium cations are of the formulae $NR^1R^2R^3R^{4+}$, $PR^1R^2R^3R^{4+}$ or $R^1R^2N=C\ R^3R^{4+}$, or $R^1R^2P=C\ R^3R^{4+}$ where $R^1$, $R^2$, $R^3$ and $R^4$, identical or different, represent hydrogen or hydrocarbyl residues containing 1 to 30 carbon atoms, with the proviso that the quaternary ammonium cation does not represent $NH_4^+$.

6. A process according to claim 4, wherein only one of $R^1$, $R^2$, $R^3$ and $R^4$ represents hydrogen.

7. A process according to claim 1, wherein the ammonium and/or phosphonium cation comprises nitrogen-containing and/or phosphorus-containing heterocycles containing 1, 2 or 3 nitrogen and/or phosphorus atoms, in which the heterocycles are constituted by 4 to 10 atoms.

8. A process according to claim 7, wherein the heterocycles contain 5 or 6 atoms.

9. A process according to claim 1, wherein the quaternary ammonium or phosphonium cation is constituted by a cation with formula:

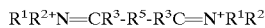

or

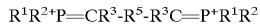

where $R^1$, $R^2$ and $R^3$, identical or different, represent hydrogen or hydrocarbyl of 1–30 carbon atoms, and $R_5$ represents an alkylene or phenylene residue.

10. A process according to claim 1, wherein the ammonium and/or phosphonium cation is selected from the group consisting of N-butylpyridinium, N-ethylpyridinium, pyridinium, 3-ethyl-1-methyl-imidazolium, 3-butyl-1-methyl-imidazolium, diethylpyrazolium, N-butyl-N-methylpyrrolidinium, trimethylphenylammonium, tetrabutyl-phosphonium and tributyl-(tetradecyl)-phosphonium.

11. A process according to claim 1, wherein the non-aqueous ionic solvent is selected from the group consisting of N-butyl pyridinium hexafluorophosphate, N-ethylpyridinium tetrafluoroborate, pyridinium fluorosulfonate, 3-butyl-1-methyl imidazolium tetrafluoroborate, 3-butyl-1-methyl-imidazolium hexafluoroantimonate, 3-butyl-1-methyl-imidazolium hexafluorophosphate, 3-butyl-1-methyl-imidazolium trifluoroacetate, 3-butyl-1-methyl-imidazolium trifluoromethylsulfonate, trimethylphenylammonium hexafluorophosphate and tetrabutylphosphonium tetrafluoroborate.

12. A process according to claim 1, wherein cobalt and/or rhodium precursor compounds of the catalyst are cobalt and/or rhodium salts and carbonyl complexes.

13. A process according to claim 12, wherein the cobalt and/or rhodium catalyst precursors are selected from the group consisting of acetylacetonates, carboxylates dicobalt-octacarbonyl, cobalt-tetracarbonyl hydride, rhodium-dicarbonyl acetylacetonate and carbonyl clusters.

14. A process according to claim 1, wherein said cobalt and/or rhodium complex is coordinated by at least one nitrogen-containing ligand selected from the group consisting of monoamines, di-, tri- and polyamines, imines, di-imines, pyridines, bipyridines, imidazoles, pyrroles and pyrazoles, said ligand comprising at least one substituent carrying an ionic function $(Q')^+(A')^-$ where at least the cation $(Q')^-$ or anion $(A')^-$ has the same chemical nature as cation $Q^+$ or anion $A^-$ of the non-aqueous ionic solvent.

15. A process according to claim 1, wherein said cobalt and/or rhodium complex is coordinated by at least one phosphorus-containing ligand selected from the group consisting of phosphines, polyphosphines, phosphine oxides and phosphites, said ligand comprising at least one substituent carrying an ionic function $(Q')^+(A')^-$ such that at least the cation $(Q')^+$ or anion $(A')^-$ has the same chemical nature as cation $Q^+$ or anion $A^-$ of the non-aqueous ionic solvent.

16. A process according to claim 1, wherein the cobalt and/or rhodium complex has a concentration in the liquid ionic solvent in the range of 0.1 moles per liter to 5 moles per liter, and the mole ratio between (a) the nitrogen-containing ligand or the phosphorus-containing ligand and (b) the cobalt and/or rhodium compound is in the range of 0.1 to 500.

17. A process according to claim 1, wherein at least one olefinically unsaturated compound selected from the group consisting of mono-olefins, di-olefins, conjugated di-olefins, olefinic compounds comprising one or more heteroatoms, olefinic compounds comprising ketone and carboxylic acid functions, undergoes the hydroformylation reaction.

18. A process according to claim 1, wherein the hydroformylation reaction is carried out with a partial pressure of hydrogen and carbon monoxide of 10:1 to 1:10, at a temperature in the range 30° C. to 200° C. and at a pressure in the range 1 MPa to 20 MPa.

* * * * *

UNITED STATES PATENT AND TRADEMARK OFFICE
CERTIFICATE OF CORRECTION

PATENT NO. : 6,410,799 B1
DATED : June 25, 2002
INVENTOR(S) : Frédéric Favre, et al.

It is certified that error appears in the above-identified patent and that said Letters Patent is hereby corrected as shown below:

<u>Column 9,</u>
Line 23, reads "$R^3R^{4+}$," should read -- "$R^3R^{4+}$, or --

Signed and Sealed this

First Day of June, 2004

JON W. DUDAS
*Acting Director of the United States Patent and Trademark Office*